United States Patent

Cheng

[11] Patent Number: 4,750,903
[45] Date of Patent: Jun. 14, 1988

[54] ARTIFICIAL HEART

[76] Inventor: Kevin K. Cheng, 1411 W. Impala Ave., Mesa, Ariz. 85202

[21] Appl. No.: 637

[22] Filed: Jan. 5, 1987

[51] Int. Cl.$^4$ .............................................. A61F 2/22
[52] U.S. Cl. ..................................................... 623/3
[58] Field of Search ........................... 623/3; 128/1 D

[56] References Cited

U.S. PATENT DOCUMENTS

| | | | |
|---|---|---|---|
| 4,058,857 | 11/1977 | Runge et al. | 623/3 |
| 4,557,673 | 12/1985 | Chen et al. | 623/3 |
| 4,648,877 | 3/1987 | Lundbach | 623/3 |

Primary Examiner—Richard J. Apley
Assistant Examiner—James Prizant
Attorney, Agent, or Firm—LaValle D. Ptak

[57] ABSTRACT

An artificial heart is made of a pair of substantially seamless, polyurethane rigid outer housings each having a shape approximating the combined outer shape of a natural cardiac ventricle and its associated auricle, with the bases of each of the housings being bonded together. Each of the outer housings includes a flexible bladder contained within the housing and having an expanded shape approximating the shape of the outer housing. This bladder is spaced from the interior surface of each of the housings a predetermined distance and the lower perimeter of the bladder is attached to the respective base. The bladder in each of the housings is attached at a point opposite the base to the interior of the housing, and a provision is made for expanding and collapsing the bladder under the control of fluid supplied to and removed from the region contained within the bladder between the bladder and the base in each housing. Each housing also is provided with one-way input and one-way output check valve openings for connection, respectively, to the veins and arteries which normally return blood to and convey blood from the heart.

42 Claims, 7 Drawing Sheets

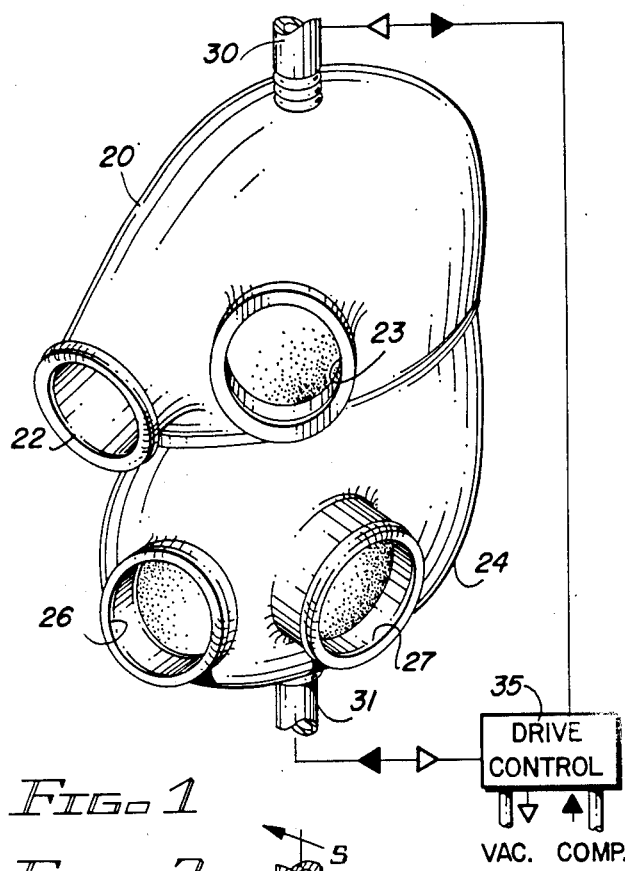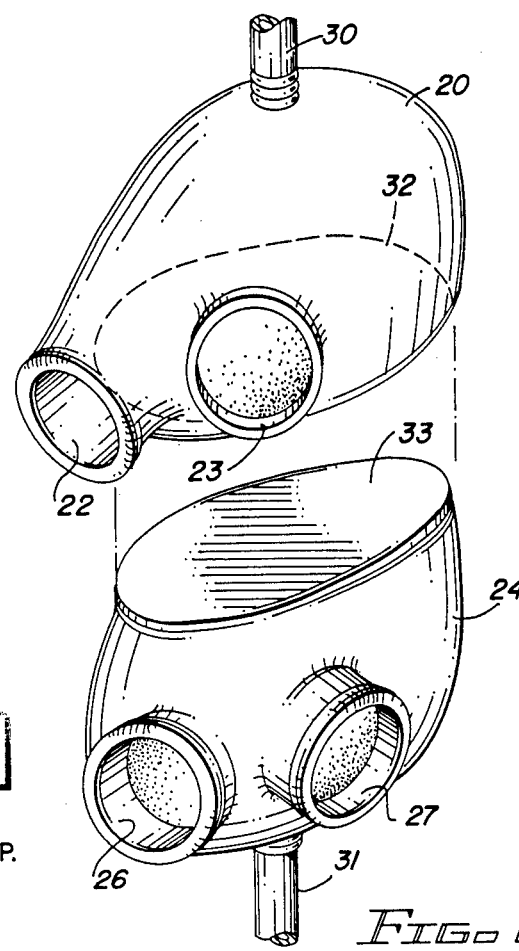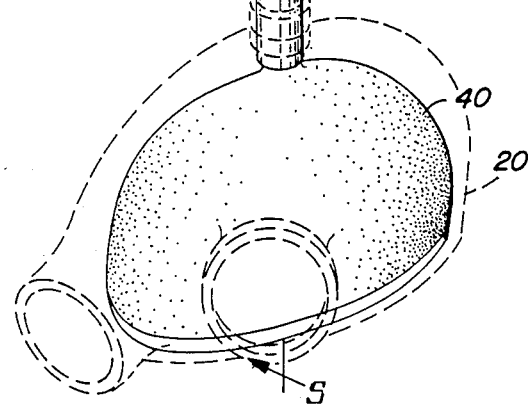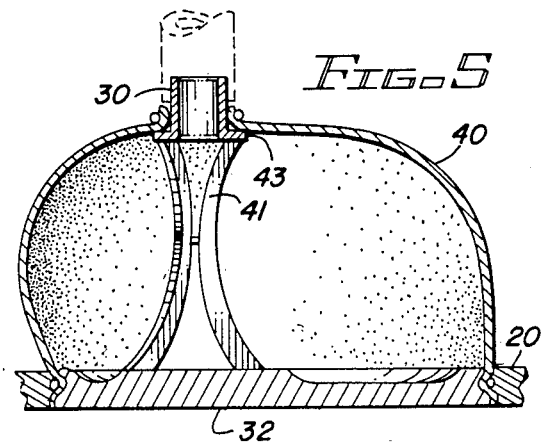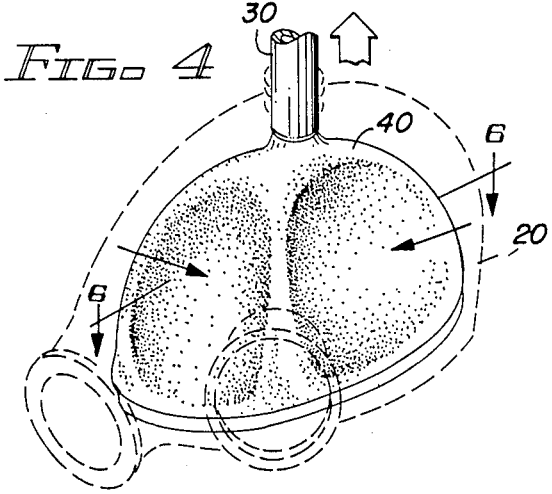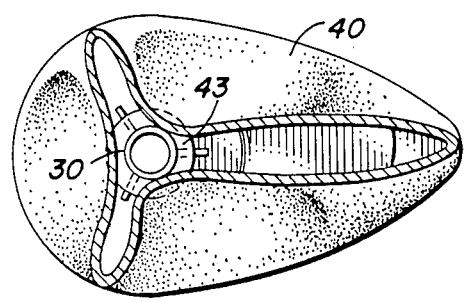

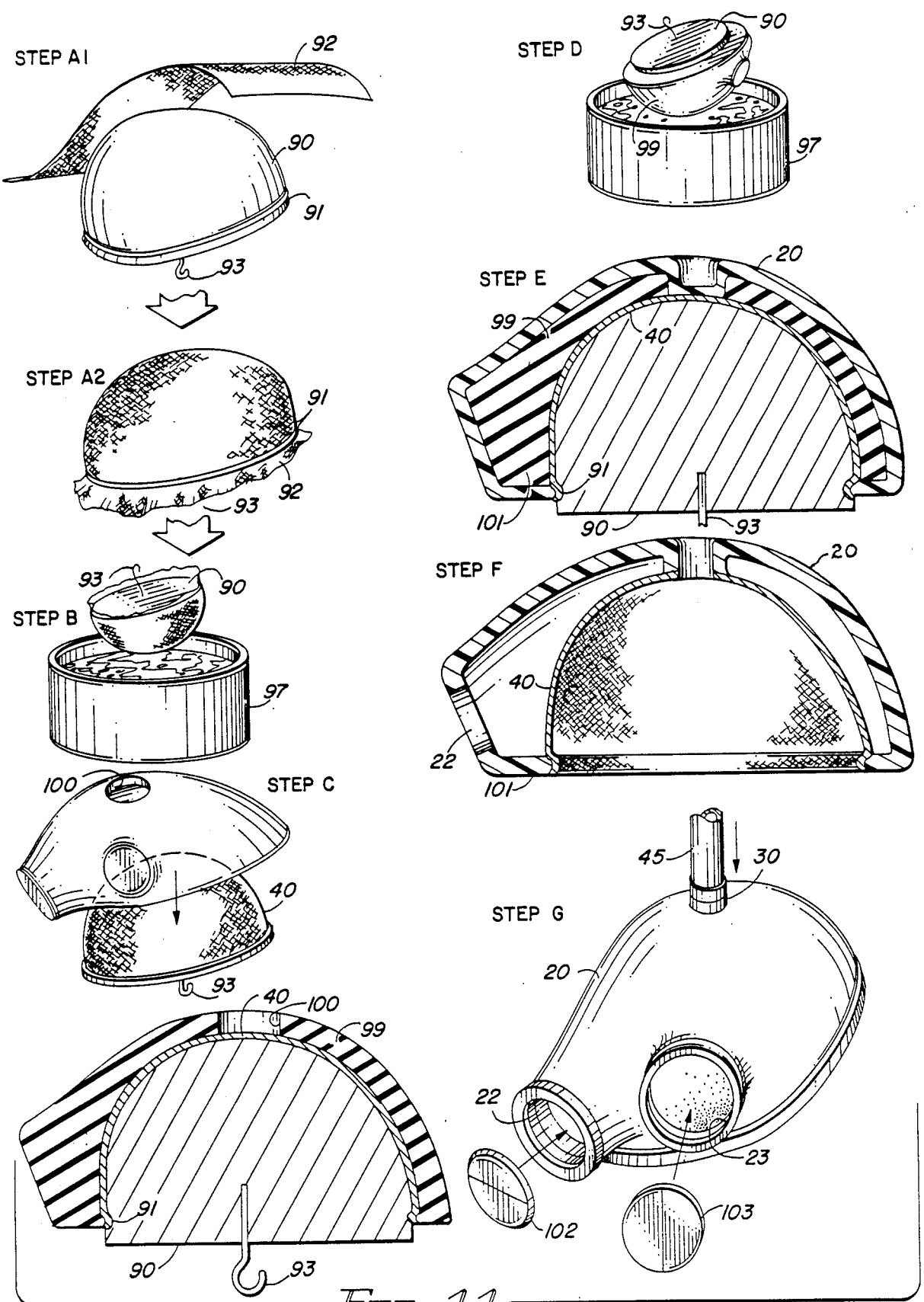

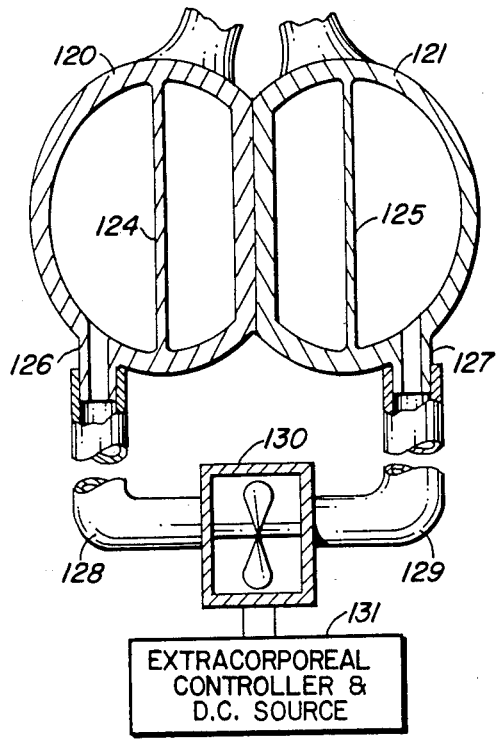
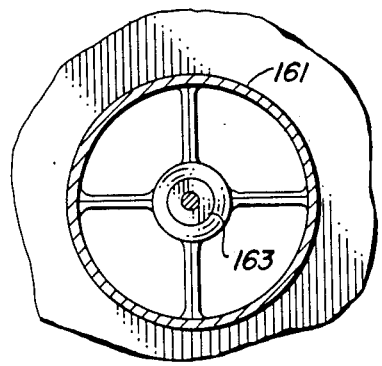
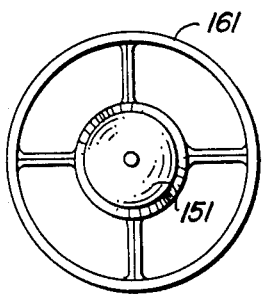
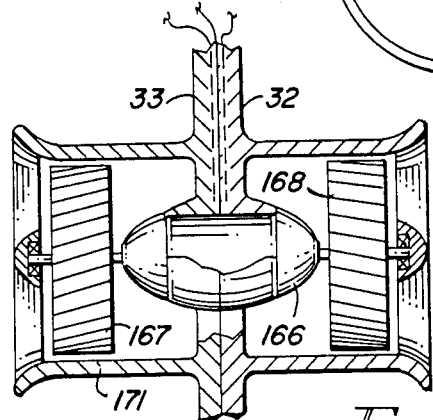
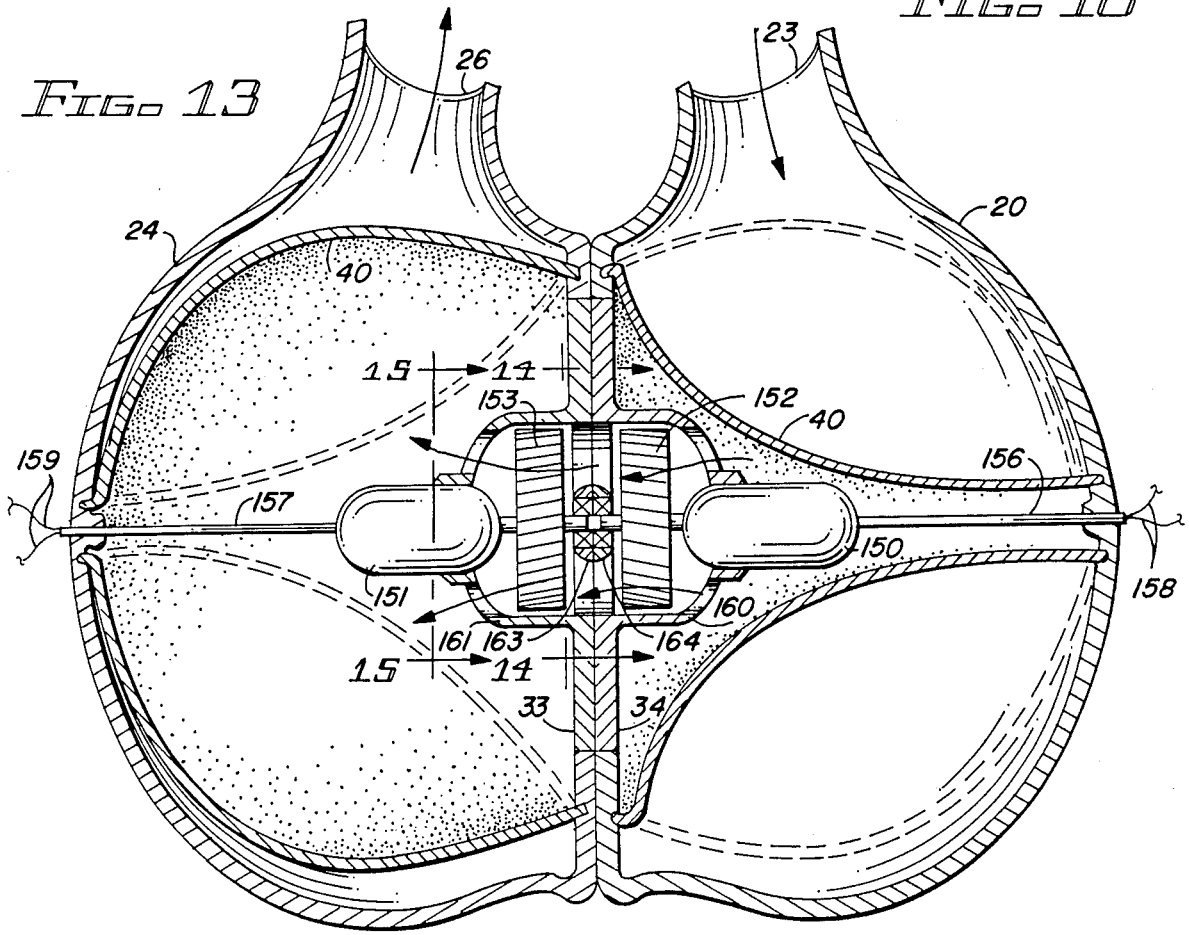

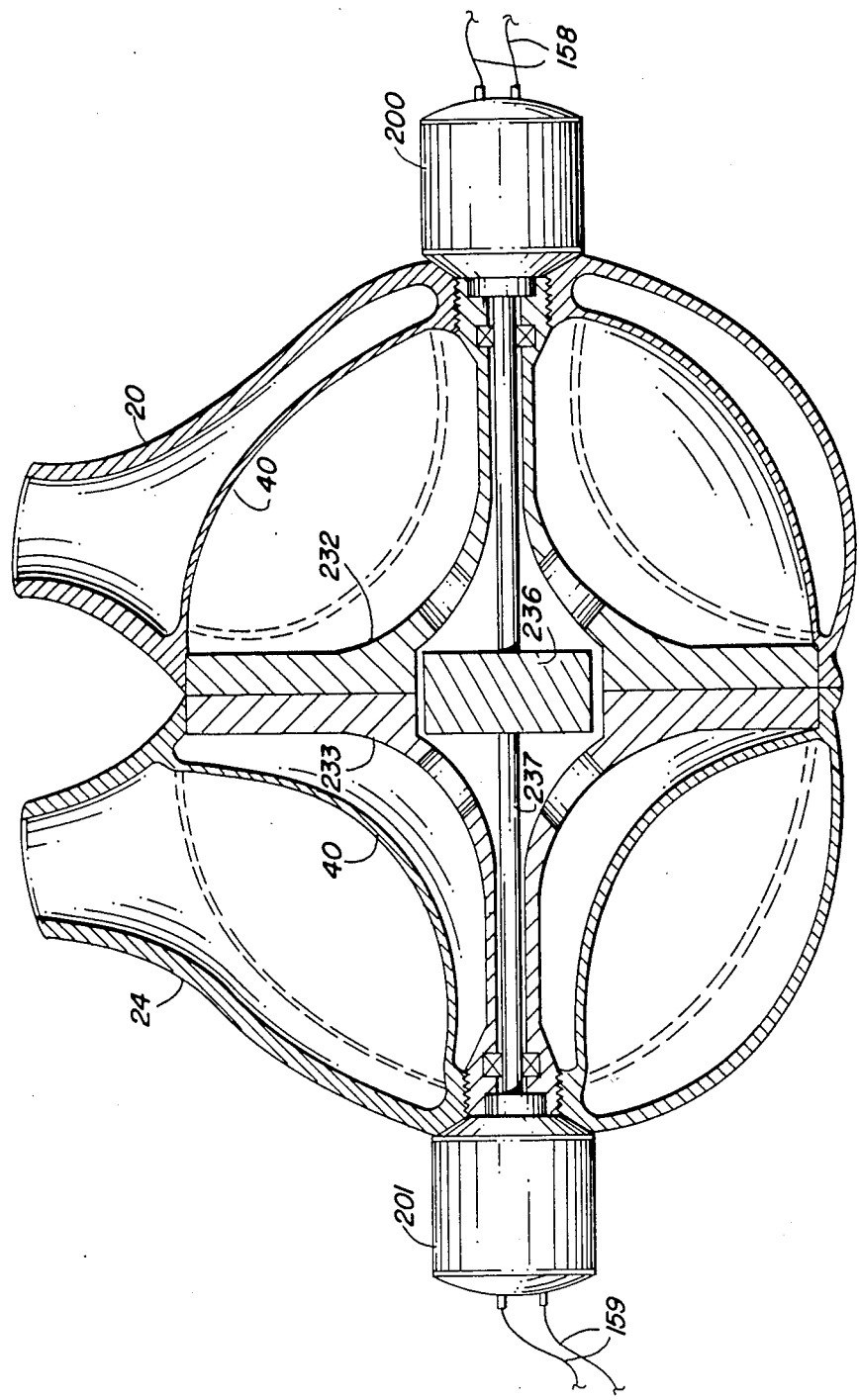

ARTIFICIAL HEART

BACKGROUND

In recent years, the field of surgical medicine has taken profound strides in the replacement of diseased or damaged natural organs with healthy organs from human donors. Typically, the donor organs are obtained as a result of the accidental death of the organ donor. These transplants have become relatively commonplace and liver and heart transplants are a viable medical option in the treatment of liver and heart disease. Transplant surgery is complicated and expensive, but it certainly has passed out of the purely experimental stage of development into a place of an acceptable medical alternative to other forms of treatment. In many cases, particularly where a weak and failing heart is involved, a heart transplant is the only meaningful way to extend the life expendency of the recipient from little or no life expendency to an additional life expendency which is measured in terms of years.

As advanced as organ transplant surgery has become, particularly heart transplant surgery a fundamental limiting problem with such surgery is always present. In every heart transplant, a donor must die that the recipient can live. There are a limited number of donor hearts available at any given time. In most cases, the proposed recipient is in critical condition; and a relatively narrow time frame, exists during which a successful heart transplant can be effected. Frequently, no donor heart is available during this time frame and the potential recipient dies of heart failure.

Temporary life support for a patient whose heart has failed is available from ex-vivo heart-lung machines. Such machines remove the blood from the body of the patient and provide the necessary carbon dioxide/oxygen exchange prior to returning the oxygen laden blood to the patient. Substantial trauma results in such machines which produce thrombosis of the blood cells. The quality of life experienced by a patient on such a machine is certainly one which would necessarily be classified as poor and cannot be sustained indefinitely.

In an effort to fill the void existing as a result of the limited availability of natural human hearts for transplant and the serious shortcomings of heart/lung machines, development of total artificial hearts (TAH) has been undertaken. During the past decade, one design of such a total artificial heart which has met with a relatively high degree of success is a pneumatic drive "diaphragm" artificial heart design. Currently, one of the more popular hearts of this design is known as the "Jarvik 7" heart. Such diaphragm type artificial hearts have separate right and left ventricles made of body compatible materials of a generally spherical shape. A thin substantially semi-spherical diaphragm divides each of the ventricles of the housing into two compartments. One of the compartments in each ventricle has a port in it for attachment to pneumatic drive lines. The other compartment in each ventricle has blood inlet and blood outlet ports fitted with mechanical disk valves. Segmented polyurethane is used to fabricate the surfaces of such artificial hearts which come into contact with blood and other body tissues. Two pneumatic drive lines are connected to the ports in the respective ventricles and extend to a pneumatic drive unit. This drive unit delivers an alternating flow of positive and negative air pressure through the drive lines to the ventricles to cause alternate pushing and pulling (back and forth) movement from the diaphragm to alternately force blood out of the second compartment of one ventricle while drawing blood into the second compartment of the other ventricle and vice versa.

Two primary problems are present in such diaphragm-type artificial hearts. First, the stroke volume of the ventricle is directly related to the diameter of the diaphragm. For any given diaphragm material, the range of movement of the diaphragm between diastole and systole is directly dependent on the diameter of the diaphragm. This is referred to as "travel distance". The travel distance cannot be changed without an appropriate change in the diaphragm diameter. Consequently, the stroke volume from such an artificial heart ventricle is severely limited by the diaphragm diameter; and a small reduction in the diaphragm diameter produces a markedly reduced stroke volume.

A second limitation of diaphragm type artificial heart ventricles results from the generally spherical shape of the ventricles which form the complete artificial heart. This creates a relatively small area of contact between the two ventricles after implantation. As a result, the limited space of the thoracic cavity is inefficiently used; and, particularly for smaller patients (such as most women and men of small physical size), this results in a reduction in the stroke volume when the ventricle size is decreased for better anatomical fit.

The diaphragm type TAH's currently being used for clinical trials is the Jarvik 7. This TAH typically measures 9 centimeters from the atrial connectors to the top of the ventricles; and the combined width of both ventricles is nearly 15 centimeters, with a maximum stroke volume of approximately 100 ml. The "mini-Jarvik" is 8 centimeters high and 14 centimeters wide and has a stroke volume of 60 ml. Current clinical experience suggest that the 100 ml. stroke volume may not be adequate for a person having a thoracic cavity and body large enough to accommodate the Jarvik 7 TAH. To compensate for this relatively low stroke volume, the number of beats per minute (pulse rate) of Jarvik 7 TAH devices typically is somewhere between 100 and 130 beats per minute. This is a substantially higher pulse rate than the normal pulse rate provided by a natural human heat. The design of a Jarvik 7 diaphragm type heart, however, is such that a larger volume cannot be obtained due to the limitations of the space available in the thoracic cavity.

Another clear disadvantage of current diaphragm type TAH devices is that such devices require two relatively large diameter pneumatic drive lines extending from a pumping unit external of the body of the artificial heart within the body. These drive lines inherently increase the danger of infection where they pass through the body and also result in depression of the lungs and other vital organs where the lines connect into the artificial heart device. In addition, significant restriction of movement of the patient is involved because of the external driving machine.

It is desirable to provide a total automatic heart (TAH) which overcomes the limitations of the prior art TAH devices discussed above. More specifically, it is desirable to provide a TAH device which more closely approximates the size and shape of a natural human heart and which has a substantially higher stroke volume in proportion to the size of the ventricles than is present in known prior art TAH devices. It also is desirable to provide a TAH device which reduces the potential for thrombosis and hemolysis.

SUMMARY OF THE INVENTION

It is an object of this invention to provide an improved artificial heart.

It is an additional object of this invention to provide an improved total artificial heart (TAH).

It is another object of this invention to provide an improved total artificial heart having an increased pumping capacity.1

It is a further object of this invention to provide an improved total pumping mechanism for a total artificial heart (TAH).

It is yet an additional object of this invention to provide an improved fabrication for a total artificial heart to reduce thrombosis and hemolysis.

It is yet another object of this invention to provide an improved artificial heart with a pumping action which simulates the natural heart pumping action.

It is still another object of this invention to provide an improved total artificial heart (TAH) which does not require external pneumatic drive lines.

It is still an additional object of this invention to provide an improved artificial heart having improved anatomical fit and morphology.

In accordance with a preferred embodiment of the invention, an artificial heart unit for one ventricle includes an outer housing which has a shape approximately the combined outer shape of a natural cardiac ventricle and its associated auricle. The housing is attached to a flat base which also is adapted for attachment to a similar flat base of a mating housing. A flexible bladder is placed in the housing, and the bladder has an expanded shape which approximates the shape of the outer housing. The bladder, however, is smaller in size than the interior of the outer housing; so that it is spaced from the interior of the outer housing a predetermined distance when it is in its expanded shape. The bladder has a lower perimeter which is attached to the base. In addition, the portion of the bladder which is opposite the base is attached to the interior of the housing; so that the remaining portions of the bladder are free to expand and collapse under control of the supply and removal of fluid from the region within the interior of the bladder between the bladder and the base.

In a more specific embodiment, the housing has first and second openings through it and first and second check valves are mounted respectively in these first and second openings. The first check valve functions to admit fluid through it into the housing and the second check valve functions to permit the passage of fluid out of the housing. These first and second check valves then are connected respectively to veins and arteries corresponding to one of the ventricles of a natural human heart so that blood is pumped through the arteries and the veins in accordance with the expansion and collapse of the bladder within the housing.

BRIEF DESCRIPTION OF THE DRAWINGS

FIG. 1 is a perspective view of the exterior of a preferred embodiment of the invention;

FIG. 2 is a partially exploded view of the embodiment of FIG. 1 showing the mating components which are connected together to form the embodiment of FIG. 1;

FIGS. 3, 4, 5 and 6 illustrate details of the embodiment of FIGS. 1 and 2;

FIG. 11 graphically illustrates various steps in the fabrication of a preferred embodiment of the invention as illustrated in the flow diagram of FIG. 8;

FIG. 12 illustrates the cross-sectional view of a prior art device;

FIG. 13 illustrates another embodiment of the invention;

FIGS. 14 and 15 illustrates additional details of the embodiment of FIG. 13;

FIGS. 16 and 17 show additional variations of the embodiment of FIG. 13; and

FIG. 17 illustrates additional features useful with the embodiment of FIG. 13; and FIG. 18 shows an additional embodiment of the invention.

DETAILED DESCRIPTION

Figure 7:
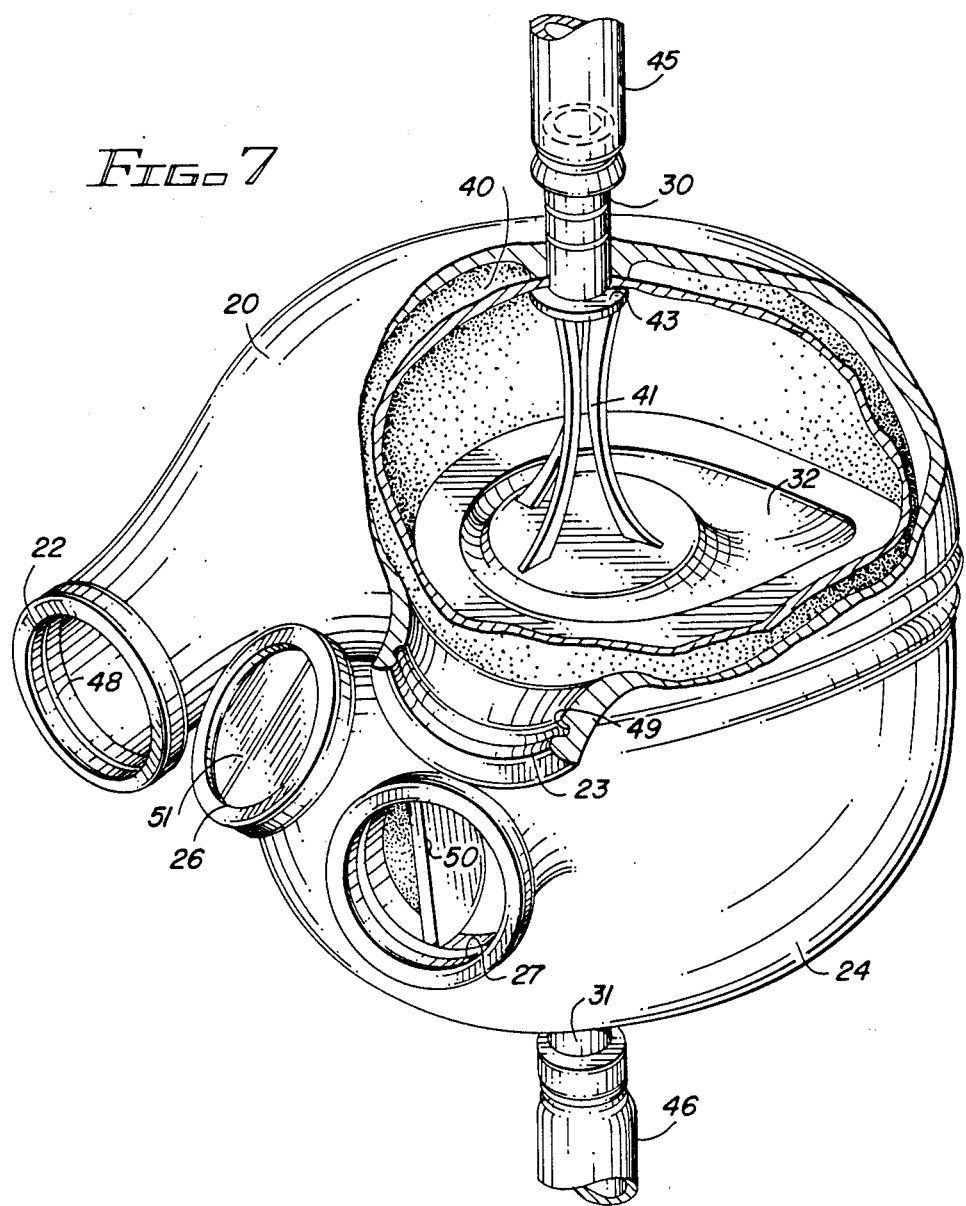
FIG. 7 is a partially cut-away view of the embodiment of FIGS. 1 and 2 showing additional features of the construction.

Reference now should be made to the drawings, in which the same reference numbers are used throughout the different figures to designate the same or similar components. A preferred embodiment of the invention is illustrated in FIG. 1 which is a three dimensional representation of a fully implantable, total artificial heart (TAH) which may be utilized to replace irrepairable human hearts. The artificial heart of FIG. 1 differs considerably from prior art structures with respect to the overall shape of the artificial heart which approximates closely the shape of a natural human heart. As a result, a relatively low profile (as measured from the front to back of the thoracic cavity) is achieved; so that the artificial heart has a wider range of anatomical fit in the human percardium. In addition, by virtue of a unique flexible pumping bladder, sufficient cardiac output is obtained to support the patient with a pumping pulse rate comparable to the normal pulse rate of a healthy human heart.

The artificial heart of FIG. 1 is made of two substantially similar parts or outer housings 20 and 24 which correspond, respectively, to the left oracle/left ventricle and right oracle/right ventricle as viewed from the front of the patient. In the ensuing discussion, these two housings 20 and 24 simply will be referred to as the ventricle 20 and the ventricle 24, but it should be understood that each of them individually perform the composite functions of the combined left oracle/left ventricle and right oracle/right ventricle of a normal heart. The ventricle 20 has an opening and valve seat 22 formed in it for connection to the aorta and another opening and valve seat 23 for connection to the pulmonary veins which normally return blood to the left oracle of the heart. Similarly, the ventricle 24 has an opening and valve seat 26 in it for connection to the pulmonary artery and an opening and valve seat 27 for connection to the systemic veins for returning blood from the body. It is noted that arteries which are connected to the openings/valve seats 22 and 26 convey blood from the artificial heart shown in FIG. 1 whereas the veins which are connected to the openings/valve seats 23 and 27 return blood to the artificial heart.

The artificial heart is operated in a manner which duplicates, to as great an extent as possible, the pumping action of a normal human heart. Consequently, the two housing ventricles 20 and 24 essentially function 180° out of phase with one another. This is accomplished in the embodiment shown in FIG. 1 by alternately supplying air under positive pressure to a pumping bladder in one of the ventricles 20 and 24, while removing air under negative pressure from the other and viceversa. This is illustrated by means of the connectors 30 and 31 coupled through suitable hoses (not shown) in FIGS. 1 and 2 to a drive control 35, which in turn produces the alternating positive and negative air pressure from a source (also not shown) at a rate adjusted to provide the necessary proper physiological functions in the patient in which the artificial heart of FIG. 1 is installed. Suitable air pumps for accomplishing this purpose are known and such known pumps and the control units for them may be employed with the artificial heart illustrated in FIG. 1.

FIG. 2 illustrates the modular construction of the artificial heart shown in FIG. 1 and shows the manner in which each of the ventricles 20 and 24 initially are fabricated as separate housings. Each of these housings is of a generally egg-shaped configuration, and the ventricle 20 has a flat egg-shaped bottom 32 which encloses the chambers of the ventricle 20 and the ventricle 24 has a corresponding flat egg-shaped bottom 33 which encloses the chambers of the ventricle 24. Typically, the ventricle 20 and 24 are made of polyurethane which has been found to be physiologically compatible with human beings and produces no adverse effects when blood comes into contact with polyurethane surfaces.

Reference should be made to FIGS. 3 through 6 which illustrate the unique high volume pumping bladder 40 used in each of the ventricles 20 and 24 to accomplish the necessary pumping action. As mentioned previously, a serious limitation of prior art "diaphragm" type artificial hearts is the limited pumping volume which can be achieved with the semi-spherical thin diaphragms housed between similarly shaped baseplates and a rigid outer housing. As a consequence, such prior are devices must be operated at a pumping rate (pulse rate) which is considerably higher than the pulse rate of a normal heart in order to achieve a comparable flow of blood through the body for any given unit of time.

The artificial heart shown in FIGS. 1 and 2 has external dimensions which are similar to that of a human heart; and to achieve the necessary pumping volume, a generally egg-shaped flexible, polyurethane bladder 40 is housed within and spaced from the interior surfaces of each of the ventricles 20 and 24. This is illustrated in FIG. 3 which shows the bladder 40 in solid lines surrounded with a dotted line representation of the ventrical 20. The bladder 40 has its bottom or open end firmly attached to and tightly sealed with the base 32 and an inward extension of the bottom of the ventricle 20 about its periphery. The manner in which this is accomplished is described subsequently in conjunction with FIG. 11. In addition, the bladder 40 has an opening at its top which communicates with the pneumatic drive line connector 30. The bladder 40 also is bonded to the inner side of the ventricle 20 in an air tight and liquid tight relationship around the opening; so that there is no interchange of air or blood through the bladder 40 or around any of its connection points.

In operation, air is supplied into the region within the bladder 40 under positive pressure to expand the bladder to the configuration shown in FIGS. 3 and 5 when expulsion of blood in the area surrounding the bladder 40 between its exterior surface and the interior of the ventricle 20 is desired. When the bladder is expanding from a collapsed condition to the condition shown in FIGS. 3 and 5, blood within the housing 20 is expelled outwardly through an open check valve in the opening valve seat 22 while at the same time a comparable check valve in the opening valve seat 23 is closed. These valves are now shown in FIGS. 1 through 6 and are described in greater detail in conjunction with FIG. 7.

When blood is to flow from the vein attached to the opening/valve seat 23, negative air pressure is applied through the line connector 30 to withdraw the air from the interior of the bladder 40, causing its collapse as shown in FIGS. 4 and 6. The collapse is essentially a three-lobed collapse as illustrated in FIGS. 4 and 6. A substantial change in volume results; and an artificial heart of the type shown in FIG. 1 having an overall height of 8 cm., a length 10.5 cm. and a combined width of the two ventricles together of 13.5 cm. produces a pumping volume per stroke of 130 ml. or more. As a consequence, a pumping rate or a pulse rate comparable to the normal pulse rate (approximately 60 beats per minute) of a healthy heart in a human being may be utilized.

FIGS. 5 and 6 also illustrate additional details of the construction of the support for the pneumatic drive connector 30 on the base 32 and the manner in which the base 32, the bottom edge of the ventricle 20 and the bladder 40 are fused together. Although the ventricle 20 and 24 are relatively rigid, additional insurance against any possible collapse when the ventricles are placed within the thoracic cavity of human being is insured by the provision of a light-weight cast Ticonium (Titanium?) frame or strut 41 which is secured at its bottom end to the base 32 prior to attachment of the base 32 into the opening in the bottom of the ventricle 20. The strut 41 is attached at its upper end to the connector 30 attached by means of a flange 43. The flange 43 is secured tightly against the interconnection of the bladder 40 and the top of the housing 20 to form a secure support for the connector 30 for the subsequent attachment of drive lines to the connector. Once the base plate 32 is in place, as illustrated in FIG. 5, it is fused to the base 20 and bladder 40. Typically, the base plates 32 and 33 are made of acrylic or reinforced polyurethane.

It is noted that the use of the flat base plates 32 and 33 for the ventricles 20 and 24 permit the two base plates to be placed flush together as illustrated in FIG. 1 to provide an improved anatomical fit. The two base plates 32 and 33 also could be combined as a single unitary base plate which serves the purpose of sealing the chambers of the two ventricals 20 and 24 in the same manner as the individual base plates 32 and 33 which are illustrated. The shape of the bladder 40 permits a more efficient utilization of the limited space available in the thoracic cavity with the stroke volume effected by the drive control and pump approximating that which is obtained from a natural human heart.

Because the bladder 40 collapses at three different points (shown most clearly in FIGS. 4 and 6) the distance of travel between systole and diastole is reduced. Of significance is the fact that the flexure of the bladder 40 at its point of maximum flexure where it is attached to the base 32, and where it is attached at the top to the fitting 30, is less than 90°. This substantially reduces the fatigue at these points or regions of maximum flexure.

The result is a prolongation of the useful life of the bladder 40.

It also should be noted that at full expansion of the bladder as illustrated in FIGS. 3 and 5, the bladder 40 never comes in contact with the inner surface of the ventricle 20. This avoids blood cell destruction which otherwise could occur if cells were trapped between the outer surface of the bladder 40 and the inner surface of the ventricle 20. The manner in which the fabrication of the ventricle 20 and the bladder 40 is accomplished to produce this result is described in conjunction with FIG. 11. The travel distance of the three separate bladder areas also is relatively short compared to the diameter of cross-sections of the bladder 40 taken in any direction.

Although the foregoing description has been primarily limited to a discussion of the ventricle 20 and the various components associated with that housing, it should be understood that a comparable bladder 40 and comparable parts also are used within the ventricle 24 which functions in exactly the same manner as the ventricle 20 and its associated bladder and other parts.

FIG. 7 is a partially cut-away detailed view of a completed assembly of the type illustrated in FIG. 1. FIG. 7 more clearly illustrates the relative locations and inter-relationships of the different parts of the artificial heart of FIG. 1. For example, air bases 45 and 46 are shown attached to the connectors 30 and 31. In addition, FIG. 7 shows in greater detail the opening/valve seats 22, 23, 26 and 27. Typically these seats are in the form of polyurethane rings which are attached to openings cut into the ventricles 20 and 24 in the locations illustrated in FIGS. 1 and 7. The seats, however, could be integrally formed with the ventricle 20 and 24, if desired.

Each of the seats includes a recessed groove (48 and 49 for the seats 22 and 23 respectively) into which suitable check valves are mounted. Two such valves 50 and 51 are shown mounted respectively in the openings 27 and 26 of the ventricle 24. Valves of this type have been used in artificial hearts with considerable success and comprise a pair of half-circular members which are supported and hinged at the center of each of the openings. The valve 50 opens inwardly to admit the return of blood from the vein to which it is attached to the chambers surrounding the bladder 40 within the ventricle housing 24 upon collapse of the bladder. Similarly, the valve 51 is mounted to open in the opposite direction to permit passage of blood outwardly through the opening 26 upon expansion of the bladder 40 within the ventricle housing 24. When blood is entering the housing 24, the check valve 51 is closed; and when blood is leaving the housing 24 the check valve 50 is closed. Other types of valve arrangements may be used, but the one illustrated in FIG. 7 has been supplied by the St. Jude Company for use in artificial hearts and have been successfully operated with reduced thrombogenicity.

Figure 9:
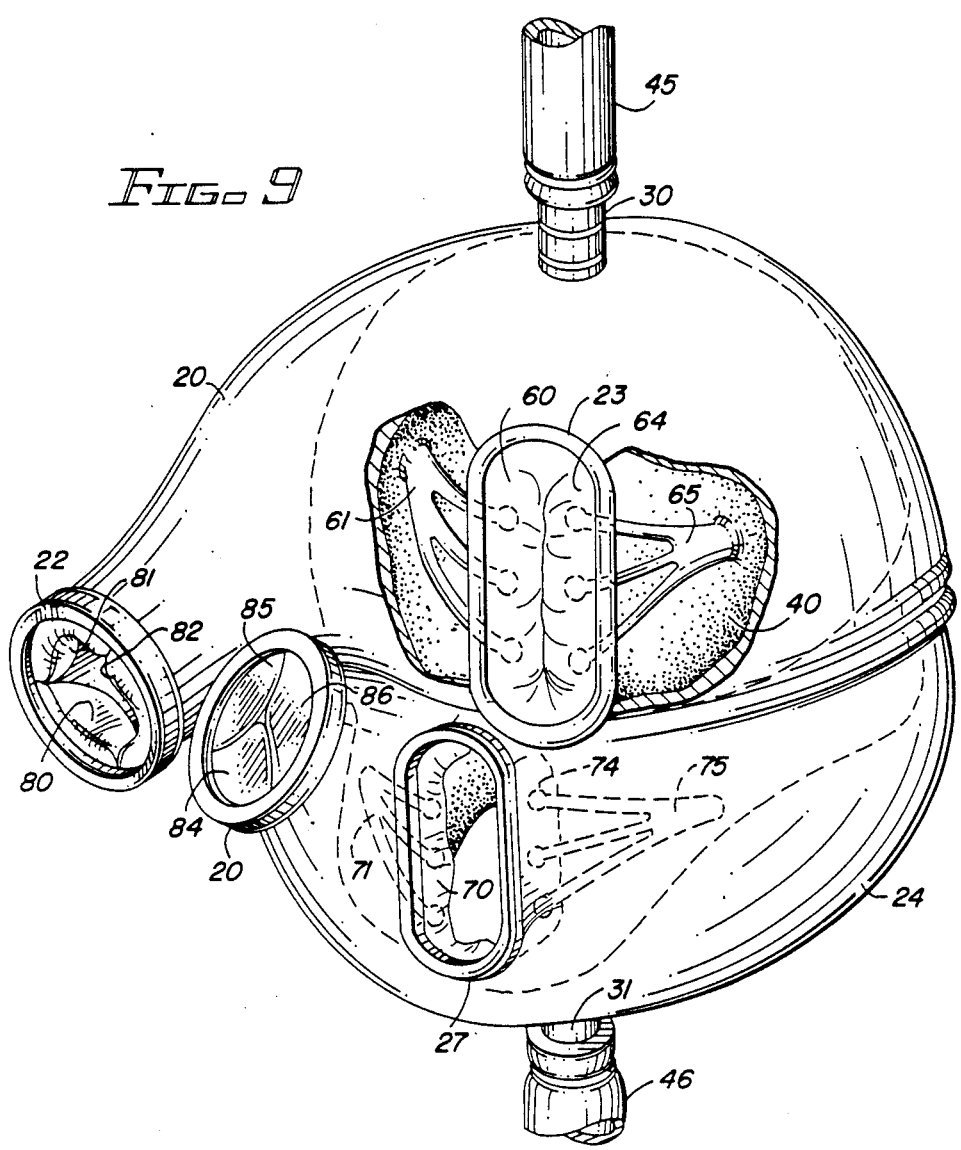
FIG. 9 is a partially cut-away view of another embodiment of the invention.
Figure 10A:
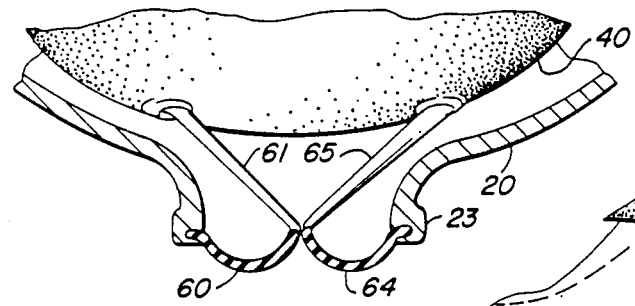
FIGS. 10A and 10B illustrate details of the operation of features of the embodiment of FIG. 9.
Figure 10B:
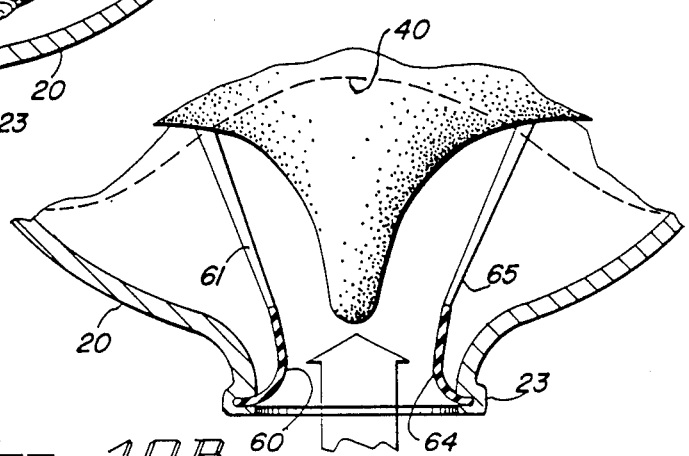

Reference now should be made to FIGS. 9, 10A, and 10B which illustrate a the different type of valve arrangement which may be utilized in place of the one shown in FIG. 7. In all other respects, the artificial heart structure of the embodiment shown in FIG. 9 is the same as the one described previously in conjunction with FIGS. 1 through 7. In the embodiment shown in FIGS. 9, 10A and 10B the rigid, semi-circular hinged valves are shown as being replaced by flexible polyurethane valves which functionally resemble more closely the natural valves present in a human heart. Because of the utilization of the bladders 40 which collapse at three different points, it is possible to construct the valves in the openings 23 and 27 connected to the return veins, to be opened by the collapse of the respective bladders 40 within the housings 20 and 24 and to be closed directly through the action of the expansion of the bladders 40 within the housings 20 and 24.

At any given time, the valves in the openings 23 and 27 operate with one of these valves open while the other is closed and vice-versa due to the alternate phase pumping action between the ventricles 20 and 24, as described previously. The openings 23 and 27 are made somewhat elongated in shape. Suitable couplers for coupling these openings to blood vessels having a substantially circular cross-section then are applied to these openings. The details of such couplers are not shown since relatively straight forward techniques which already have been used in conjunction with previous artificial heart implantations may be employed.

The valve in the opening 23 comprises two elongated flexible sections 60 and 64. Similarly, the valve in the opening 27 comprises elongated sections 70 and 74. FIGS. 10A and 10B illustrate cross-sections through the valve in the opening 23 showing it in its closed position and open positions, respectively. In the closed position of the vlave 60/64, illustrated in FIGS. 9 and 10A, two sets of relatively rigid polyurethane tendons 61 and 65 extend from the ends of the valve halves 60 and 64 near their point of contact in the center of the opening 23 to points of attachment on the bladder 40. When the bladder 40 is in its expanded position (for expelling blood through the arterial opening 22, these tendons 61 and 65 push the edges of the valve halves 60 and 64 toward one another into engagement to close the valve as illustrated in FIG. 10A. This is the systolic position of the valve. In the diasystolic position, the bladder 40 collapses and pulls the tendons 61 and 65 inwardly as shown in FIG. 10B. This pulls the ends of the valve members 60 and 64 inwardly, as illustrated in FIG. 10B, to permit the inflow of blood into the chamber surrounding the bladder. A similar operation takes place within the ventricle 24 with respect to the valve members 70 and 74 which are operated by polyurethane tendons 71 and 75 in a manner identical to the operation of the valve in the ventricle 20.

Tri-lobed check valves are provided in the arterial openings 22 and 26 of the embodiment shown in FIG. 9. Once again polyurethane overlapping lobes 80, 81, and 82 are used in the opening 22 and similar lobes 84, 85, and 86 are employed in the opening 26 in the ventrical 24. These lobes open outwardly under pressure to permit blood to be pumped outwardly through them as the bladder 40 within the respective ventricle 20 or 24 expands, and the lobes fold inwardly against one another in an overlapping relationship to block the reverse flow of blood when the bladder 40 within the respective ventricle 20 or 24 collapses to the position shown in FIGS. 4 and 6. In all other respects, the embodiment of FIG. 9 operates in the same manner as the embodiment described in FIGS. 1 through 7.

Figure 8:
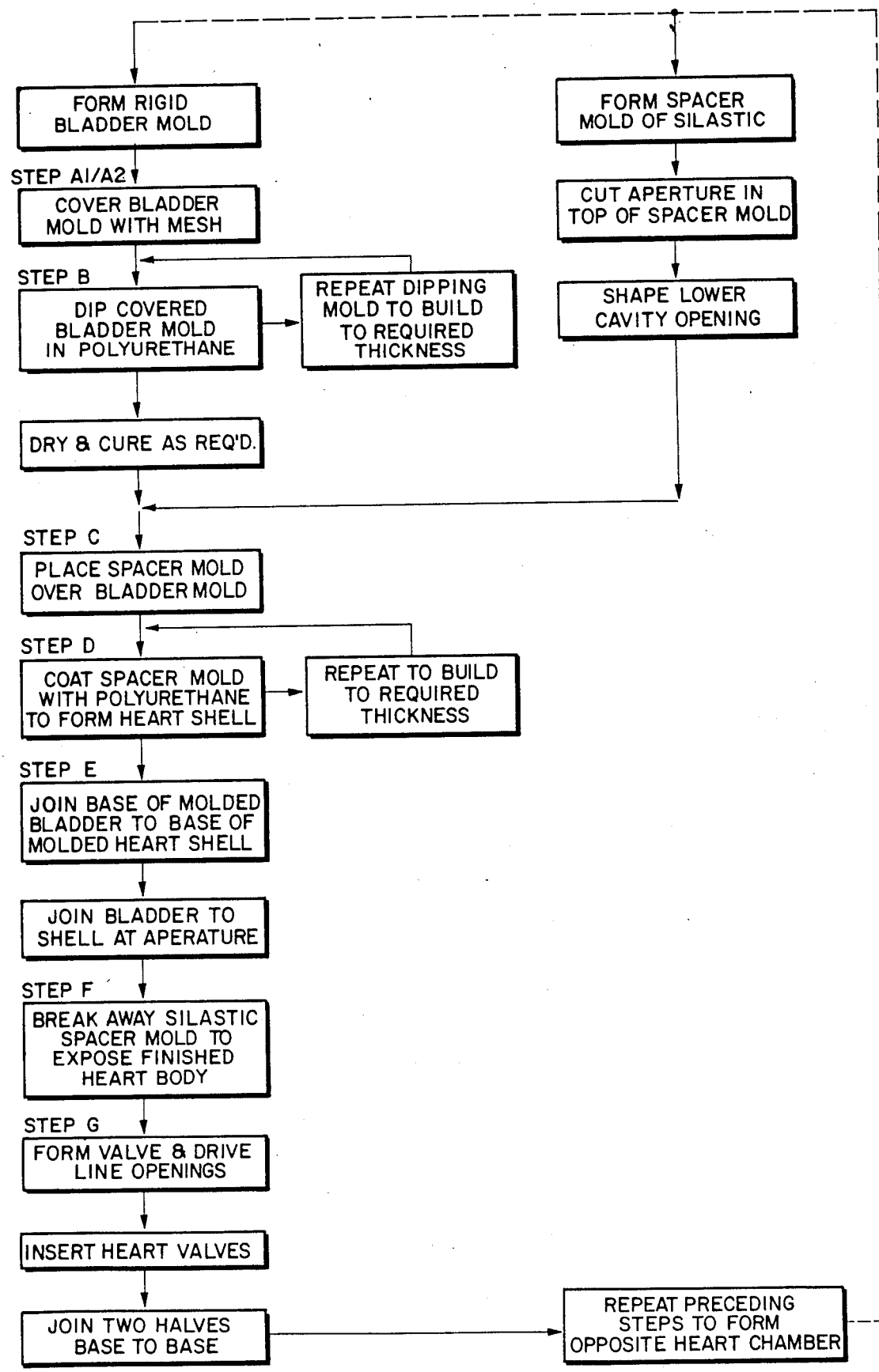
FIG. 8 is a flow diagram of the method of fabrication of the embodiment of FIGS. 1 through 7.

Reference now should be made to FIGS. 8 and 11 which illustrate a preferred method of fabricating the housing and bladder for each ventricle 20 and 24 of the artificial heart described above. A spacer technique of fabrication is employed for the purpose of developing a ventricle which is a seamless single unit. This significantly reduces the potential for failure of the ventricle due to fabrication errors. In addition, the one piece fabrication also allows for relatively simple modification of the fabrication procedure to permit design changes in ventricles. Since joints and seams tend to wear and fail more readily than solid or seamless parts, the elimination of seams inherently should result in increased durability.

In the fabrication of both the ventricles 20 and 24 and the bladders 40 contained within these ventricles, segmented polyurethane material is selected. This material has high strength versatility and high bio-compatability with the blood and the human body.

The various steps which are employed are outlined in a flow chart in FIG. 8, which illustrates the features of the method shown diagrammatically in FIG. 11. Utilizing this method produces a single piece construction which has no joints or seams in it. By eliminating the need to secure or reinforced joints, the fabrication process is simplified. In addition, joints and seams also can be sources of turbulence or increased shear in a finished artificial heart product which results in increased thrombogenicity and/or hemolysis. The one piece fabrication which is utilized in the method described in conjunction with FIGS. 8 and 11 creates a smooth blood contact surface both on the bladder 40 and on the internal surfaces of the ventricle 20 and 24. The only joints in the structure are between the valves and the outer ventricles 20 and 24. As stated previously, the bladders and outer housings are mode of polyurethane since it has high strength to weight ratio, and may be made either in a highly flexible configuration (for the bladders 40) or semi-rigid (for the ventricles 20 and 24).

The first step in the fabrication of the total artificial heart of all of the embodiments is the construction of molds for the bladders 40 to be placed within each of the ventricles 20 and 24. The bladder mold preferably is made of standard dental die stone 90 and is formed with a groove 91 around its periphery near the base. The flat bottom of the bladder mold 90 has a wire hook 93 attached to it for use in subsequent steps of the method. In Step A1 (FIG. 11) the bladder mold 90 is next covered with a sheet of reinforcing nylon mesh 92. The mesh 92 may be secured on the mold 90 by means of a suitable fastener such as a nylon thread or the like.

The covered bladder mold 90 then is turned over as shown in Step B of FIG. 11 and is dipped in a 12.5% segmented polyurethane solution in a vat 97. The dipping process is done slowly, and the mold 90 is withdrawn slowly to avoid air bubbles and unevenness. The mold is dried for a minimum of 40 minutes and then is repeatedly dipped to build the bladder being formed to the required thickness. The mold is dried for a minimum of 40 minutes between each coat. In an alternative form of construction, the mold 90 may be dipped in the polyurethane solution several times prior to the applicatioan of the nylon mesh 92 and then dipped two or three more times following the application of the mesh. This causes the reinforcing nylon mesh 92 to be sandwiched between polyurethane coats. The total number of polyurethane layers for the formation of the bladders 40 in this manner is generally 4 or 5 coats. After the final coat is applied, the bladder, on the mold 90 is permitted to dry and cure as required by the materials used.

An additional spacer mold also is made of silastic plastic for placement over the mold 90 after the bladder 40 has been formed on the surface of the mold 90. To accomplish this, a negative impression cast is made of the outer hosuings 20 and 24 using denstal die stone. Separate casting molds must be made for both the ventricles 20 and 24 to insure proper placement of the bladder inlet and outlets as necessitated by the human anatomy. A two piece casting mold is employed to form the outer ventricle housings.

After the casting of the outer housing mold is formed, the bladder mold 90 with the bladder 40 formed on it is positioned in the casting mold. Prior to the pouring of silastic material into the casting mold, these molds are sprayed with a thin coat of silicon lubricant which acts a release agent to permit removal of the silastic free from adherence to the molds. The bladder mold 40 is spaced from the interior surface of the casting mold; and when it is in the proper position, silastic, which may be Dow Corning 3110 R.T.V. Silicon Rubber, is poured into the casting mold to create a silicon "spacer" 99. This spacer 99 insures a space between the bladder 40 and the inner wall of the outer ventricle housing in the finished total artificial heart.

The spacer and bladder mold 90 are removed as a unit from the casting mold and a ⅜" hole 100 is created in the spacer 99 at the location of the air line connection (30 or 31 of FIG. 1) when the silicon has cured. This entire assembly then is dipped in the polyurethane solution in the tank 97, as illustrated in Step D of FIG. 11, a substantial number of times (35 times or so) allowing drying time between each dip. This forms a firm outer ventricl housing (20 or 24) around the bladder 40 and seals the respective housing and bladder together at the base 101 in the region of groove 91. It should be noted that during this process the mold 90 extends beyond the base which is formed around the bottom of the silicon spacer (as viewd at the lower left of FIG. 11) to permit the silicon to flow around the bottom of the silastic spacer to bond with the bladder 40 where it is indented into the groove 91 on the bladder mold 90.

Next (Step F) the blood inlet and outlet openings (for example 22 and 23 for ventricle housing 20) are opened or cut through the ventricle into the silastic spacer 99; and the spacer is carefully removed through these openings. The material of the spacer 99 is quite flexible and very elastic and may be pulled through the openings 22 and 23 in one or two complete chunks. Prior to this step, or subsequent to it, the mold 90 is removed simply by pulling it downardly in the direction of the bottom of the structure shown in Step F of FIG. 11 to leave the bladder 40 secured at its lower edge to the inwardly turned lip 101 on the housing 20.

Once all of the pieces of the silastic spacer 99 have been removed from the space between the inner surface of the ventricle 20 (or 24) and the outer surface of the bladder 40, the space formerly occupied by the spacer 99 is washed thoroughly in distilled water to remove all of the silicon rubber residue. As shown in Step E in FIG. 11, the air port is completely sealed with the polyurethane forming the outer housing 20. Consequently, this port must be reopened, but it is cut to a smaller diameter than the diameter of the hole 110 through the spacer 99. This smaller diameter is selected to be equal to the outer diameter of the connector 30 (or 31); so that the connector 30 (or 31) may be passed through the openign from within the mold 40.

Next the base plate 32 (FIG. 5) and the center strut 41 (previously connected together) are placed in the opening formerly occupied by the mold 90, with the connector 30 passing through the hole in the top of bladder 40 (see Step F of FIG. 11) until the flange 43 securely engages the inner side of the bladder 40. As mentioned previously, the base plate 32 is fabricated of a clear acrylic which is sanded smooth and which has the strut 41 attached centrally to it. The base assembly is dipped twice in polyurethane prior to attachment to the ventricle to promote a good seal to the ventricle 20 or 24 with which it is used. The joints around the perimeter of the base 32 and around the outside of the strut orifice where the connector 30 passes through the housing are sealed using polyurethane applied with a syringe.

After the unit is complete, the interior of the bladder 40 communicates through the opening in the connector 30, but is completely isolated from the chamber between the outside of the bladder 40 and the interior of the ventricle 20 or 24. Thus, separate pneumatic and blood chambers are formed. Air which is directed through the connector 30 (or 31) to the interior of the bladder 40 (the pneumatic chamber) is isolated by the bladder 40 from the blood chamber which is located between the outside of the bladder 40 and the interior surface of the ventricle 20 or 24.

The blood inlet and outlet openings 23 and 23, respectively, for the ventricle 20 (or 27 and 26, respectively, for the ventricle 24) are sized to hold the valves as described previously. Typically the inlets or vein connections use valves having a 29 ml. diameter and the outflow or aortic and pulmonary artery valves are 27 ml. in diameter. The valves 102 and 103 (FIG. 11) are placed into the openings 22 and 23 in the ventricle 20; and the previously described valves 50 and 51 are placed, respectively, in the opening 27 and 26 in the ventricle housing 24. This may be done with any suitable construction techniques and the valves are sealed in place utilizing biocompatable materials.

Although the artificial heart which has been described above is a highly efficient, compact device which is well suited to implantation in place of an irrepairable natural heart, the device still violates the integrity of the skin due to the requirement for the air pressure supply lines 45 and 46 connected to an exterior pneumatic controller system. As a consequence, so long as such an external controller is required, a major disadvantage of prior art diaphragm type artificial hearts continues to be present. A typical prior art heart of this type is shown for comparison purposes in FIG. 12. The device shown in cross-section in FIG. 12 constitutes an illustration of prior art diaphragm hearts such as the Jarvik 7 art and the like. Such devices comprise a pair of interconnected hemispherical ventrical housings 120 and 121 in which a pair of semi-spherical or circular diaphragms 124 and 125 are mounted. Fittings 126 and 127 are provided for connection to a pneumatic control system, and plastic pneumatic supply lines 128 and 129 connect these fittings with a reversible pneumatic pump 120. The lines 128 and 129 are copmarable to the lines 45 and 46 described above in conjunction with embodiments of this invention. A suitable controller and direct current source 131 is used to control the operation of the pneumatic pump 130. Because of the limited pumping capacity of prior art diaphragm type artificial hearts, it is not feasible to incorporate the pumping mechanism within the structure of the artificial heart itself. If this were done, the overall external dimensions of the resultant artificial heart would be too large to fit into the thoracic cavity of a patient. Consequently, diaphragm type artificial hearts are severely limited in usefulness. The large external drive controllers 131 and pumpts 130, together with the tubing that connects to the patient significantly restricts the mobility of the patient. In addition, since the tubes 128 and 129 violate the integrity of the skin, these tubes serve as conduits for infection.

Because of the highly efficient, high volume pumping action which is obtained by use of the bladder 40, it is possible to mount the pump and drive mechanism for the pump internally in the body. One structure for accomplishing this is illustrated in FIG. 13. The external ventricles 20 and 24 along with the bladders 40 mounted within these ventricles are constructed in the same manner as in the embodiments described previously. No external opening for a connection to a pneumatic system, however, is provided. Instead, the base plate 32 and 33 have an enlarged central opeing through them and preferably are formed with open frameworks 160 and 161 which support a pair of small electric motors 150 and 151 respectively. The motors, in turn, rotate a corresponding pair of impellers 152 and 153 in opposite directions and are alternately turned on and off by means of electric signals applied over leads 158 and 159 connected through sealed supply tubes 156 and 157 to the motors 150 and 151, respectively.

The logic circuitry for controlling the operation of the motors may be located externally of the body, with only the leads 158 and 159 violating the skin integrity or, as described subsequently, may be implanted entirely within the body. The motor 150 rotates its associated impeller 152 in a suitable bearing 164 mounted in the base plate 32. Similarly, the motor 151 rotates the impeller 153 which is independently mounted in a bearing 163 in the base plate 33.

When the motor 150 is operated, the working fluid, which is free to communicate betweenthe interiors of both bladders 40, is driven from the interior of the bladder 40 in the ventricle 20 to fill the interior of the bladder 40 within the ventricle 24. The motor 150 then is turned off and the motor 151 is turned on. The motor 151 then drives the working fluid from within the bladder 40 located in the ventricle 24 into the bladder 40 located within the ventricle 20. This alternating operation causes the bladders 40 to be filled and to collapse in the same manner described previously for the externally operated pneumatic system. Consequently, the function of the artificial heart is the same as described previously. The mechanism, however, is entirely located within the body and the violation of the skin integrity is much less than in conjunction with the pneumatic systems which require relatively large diameter tubes to pass through the skin of the patient. FIGS. 14 and 15 are cross-sections taken along the corresponding lines of FIG. 13 to show the manner of the mounting of the bearings and motors within the respective ventricles.

FIG. 16 illustrates a variation of the embodiment shown in FIG. 13 in which single reversible motor 166 is used to drive a pair of impellers 167 and 168 to move the hydraulic fluid back and forth from the itnerior of one bladder 40 to the other in an alternating fashion.

Figure 17A:
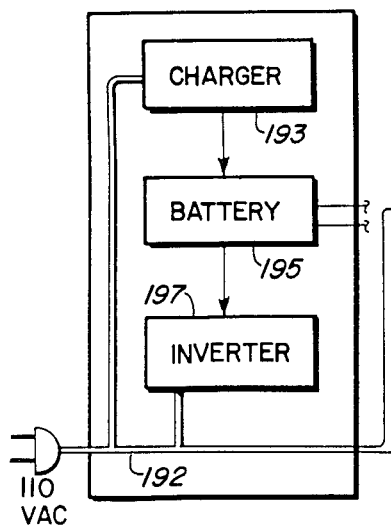
Figure 17B:
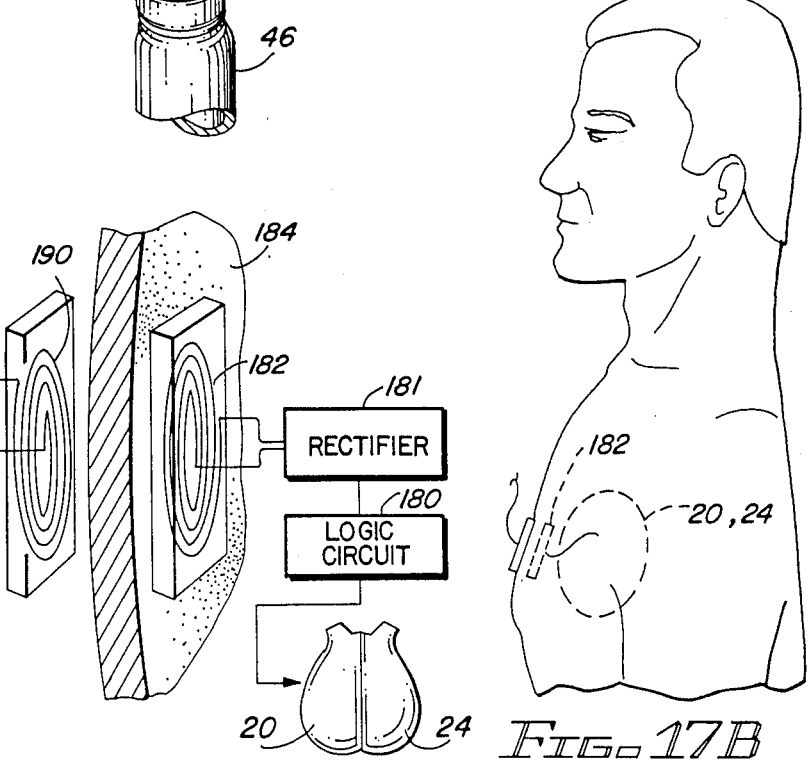

A possible technique for utilizing an internally controlled artificial heart of the type shown in FIGS. 13 through 16 without the necessity for permanent violation of the skin integrity is shown in FIGS. 17A and 17B. As illustrated, the logic circuit 180 for supplying signals to the motors (or single motor if the embodiment of FIG. 16 is used) may be mounted in a suitable position on one or both of the ventricles 20 and 24. The logic circuit 180 is supplied with operating direct current power from a rectifier 181 which is connected to a transformer secondary coil 182 mounted within the body on the inside of intact skin 184. The transformer coil 182, along with the logic circuit 180 and rectifier 181 all may be mounted on the ventricle 20 or 24. Opposite the secondary coil 182, a primary coil 190 of the transformer is affixed to the skin 184 in any suitable manner; so that the primary coil 190 is located in a flux coupling relationship with the coil 182.

Two modes of operation for applying alternating current to the coil 190 exist. The first is that the coil 190 may be attached to conventional houshold line current through a lead 192. Whenever the patient is within a room this probably is the preferred mode of operation. Any time the coil 190 is being supplied with power from the lead 192, alternating current also is applied to a battery charger 193 which receives the alternating current and converts it to a direct current used to charge a rechargeable storage battery 195. Suitable circuitry is employed; so that in the event a power failure should occur or the power supplied over the lead 192 should be interrupted for any reason, direct current from the battery 195 is applied through an inverter 197 which then supplies alternating current to the primary winding 190 of the transformer. Consequently, a continuous supply of power is available to ensure continued operation of the fully enclosed total artificial heart located within the patient's body.

Refrence now should be made to FIG. 18 which illustrates a variation of the embodiment shown in FIG. 13. Those components which are the same or similar to those in FIG. 13 are provided with the same reference numbers. The primary difference between the embodiment shown in FIG. 18 and the one in FIG. 13 is that a pair of reversible motors 200 and 201 are externally mounted and sealed to the respective ventricles 20 and 24. The position of the motors 200 and 201 is comparable to the positions of the connectors 30 and 31 of the embodiments shown in FIGS. 1 through 7. A single impeller 236 is mounted in a common opening between base members 232 and 233 which otherwise seal the bottom of the ventriles 20 and 24 in the same manner as described previously for the bases 32 and 33. Consequently, a common flow path for hydraulic fluid exists within the interiors of the bladders 40 located within each of the ventricles 20 and 24. The motors 200 and 201 are supplied with power in a manner similar to that described in conjunction with FIGS. 13 and 17. Each of the motors 200 and 201 are reversible motors, and they are run in parallel with one another. A common shaft 237 extends from each of the motors and has the impeller 236 mounted on its center. Since the motors are not located close to the impeller 236 of the axial flow pump, the cross-sectional area of the pump impeller 236 can be made larger than with the impellers of the embodiment shown in FIG. 13. Consequently, the larger impeller 236 is capable of moving more fluid at less power or less rotational speeds. In normal operation of the embodiment of the artificial hear shown in FIG. 18, the impeller 236 is driven in tandum by both motors 200 and 201. Consequently, the power consumption and the load is shared by both motors and heat rejection is more easily handled. In the event that one or the other reversible motors 200 or 201 should fail, the other motor continues to operate to drive the ipeller 236. Consequently, a fully redundant system is present.

For the fully self-contained artificial hearts of the embodiments shown in FIGS. 13 and 18, the working fluid which is transferred back and forth from the interior of one bladder 40 to the other in the ventricles 20 and 24 preferably is methyl silicon. A primary advantage of methyl silicon is its inherent corrosion resistance. Methyl silicon fluids do not appear to pose any problems for the electric motors 150 and 151 of the embodiment of the FIG. 13 which are fully submerged within the fluid. Other types of hydraulic fluid, however, may be used provided the fluid is compatible with the mechanical parts submerged within the fluid in the itnerior of the artificial heart. It should be noted that the hydraulic fluid used to expand and collapse the bladder 40 in the embodiments of FIGS. 13 and 18 does not need to be bio-compatible since it is completely isolated from any contact with any part of the body or the blood of the patient in which the heart is installed.

It also should be noted that in conjunction with the embodiment of FIG. 18 that no particular problems arise from the location of the motors 200 and 201 on the exteriors of the ventricles 20 and 24. The axis on which these motors are mounted extends across the chest of the patient and this dimension is not particularly critical since the small amount of additional space which is required for the motors 200 and 201 is readily accommodated by the lungs of the patient in which the heart is installed.

It is apparent that the inclusion of the motor impeller and hydraulic fluid within the embodiments of the heart shown in FIGS. 13 and 18 will result in greater wieght of the artificial heart than for the pneumatically driven devices of FIGS. 1 through 7. This additional weight should not be any problem. In the event, however, that the additional weight should cause movement of the implanted artificial heart within the body, it is possible to support the devices of FIGS. 13 and 18 by anchoring them to the skeletal structure (ribs) to prevent the moving, shifting or dropping of the device.

While the primary use envisioned for the artificial heart is as a complete substitute for a natural heart, a single ventricle 20 or 24 (one-half a heart) may also be used as a ventricle assist device for a weakened ventricle without replacement of the natural heart or any part of it. The structure of such a ventricle assist device, whether in-vivo or ex-vivo, is the same as described above for the ventricle 20 or 24.

The foreging description of the preferred embodiments made in conjunction with the various figures of the drawings is to be considered illustrative of the invention and not as limiting. Various changes and modifications will occur to those skilled in the art without departing from the true scope of the invention. For example, a variety of different types of valves may be used to control the in-flow and out-flow of the blood from the blood chambers of the various artificial heart embodiments which have been described. The particular mateiral which has been described have been utilized in working embodiments of the heart, but other materials, provided they are bio-compatible may also be employed if desired. The specific arrangements of the motors and impellers also may be varied without departing from the spirit and scope of the invention. The manner of interconnecting the ventricle housings together may be varied, and a variety of surgical techniques may be employed to connect the veins and arteries of the patient to the heart which is implanted and substituted for an irrepairable normal heart.

I claim:

1. An artificial heart unit including in combination:
    an outer housing having a shape approximating the combined outer shape of a natural cardiac ventricle and its associated auricle;

a flat base attached to said housing and adapted for attachment to a similar flat base of a mating housing;

a flexible bladder in said housing, said bladder having an expanded shape approximating the shape of said outer housing and being smaller in size than the interior of said outer housing and being spaced therefrom a predetermined distance, said bladder having a lower perimeter;

means for attaching the lower perimeter of said bladder to said base; and means for attaching said bladder to the interior of said housing at a point opposite said base, so that the remaining portions of said bladder are free to expand and collapse under control of the supply and removal of fluid from the region within the interior of said bladder between said bladder and said base.

2. The combination according to claim 1 wherein said outer housing is seamless except where said housing is attached to said base.

3. The combination according to claim 1 further including means for supplying and removing fluid to and from the interior of said bladder, said means comprising conduit passing through said outer hsouing and into the interior of said bladder at the place where said bladder is attached to the interior of said housing.

4. The combination according to claim 1 wherein said outer housing is fabricated substantially of rigid polyurethane, and said bladder is made substantially of flexible polyurethane.

5. The combination according to claim 4 wherein said bladder includes a flexible reinforcing mesh embedded in said flexible polyurethane.

6. The combination according to claim 1 wherein said means for attaching the lower perimeter of said bladder to said base comprises bonding the material of the lower perimeter of said bladder to of said base.

7. The combination according to claim 1 wherein said outer housing has first and second opeings therethrough; and further including first and second valves mounted respectively in said first and second openings, wherein said first valve functions to admit blood therethrough into said housing and said second valve functions to permit the passage of blood out of said housing.

8. The combination according to claim 7 further including coupling means for attaching an artery to said second opening and for attaching a vein to said first opening in said outer housing.

9. The combination according to claim 1 further including means for supplying and removing fluid from the interior of said bladder.

10. The combination according to claim 7 further including means for supplying and removing fluid to and from the interior of said bladder, said means comprising conduit passing through said outer housing and into the interior of said bladder at the place where said bladder is attached to the interior of said housing.

11. The combination according to claim 10 wherein said conduit comprises a drive line connector; and further including support means extending between said base and said drive line connector at the point where said bladder is attached to the interior of said housing.

12. The combination according to claim 10 wherein said outer housing is fabricated substantially of rigid polyurethane, and said bladder is made substantially of flexible polyurethane.

13. The combination according to claim 12 wherein said outer housing is seamless except where said housing is attached to said base.

14. The combination according to claim 13 wherein said bladder includes a flexible reinforcing mesh embedded in said flexible polyurethane.

15. The combination according to claim 14 wherein said means for attaching the lower perimeter of said bladder to said base comprises bonding the material of the lower perimeter of said bladder to of said base.

16. The combination according to claim 7 further including coupling means for attaching an artery to said second opening and for attaching a vein to said first opening in said outer housing.

17. The combination according to claim 16 wherein said coupling means comprise first and second cylindrical projections attached to said outer housing and surrounding said first and second openings, respectively.

18. The combination according to claim 17 wherein said outer hosuign has first and second openings therethrough; and further including first and second valves mounted respectively in said first and second openings, wherein said first valve functions to admit blood therethrough into said housing and said second valve functions to permit the passage of blood out of said housing.

19. An artificial heart including in combination:

a first outer housing having a shape approximating the combined outer shape of a natural cardiac ventricle and its associated auricle;

a first flat base attached to said first housing and adapted for attachment to a similar second flat base of a second housing;

a first flexible bladder in said first housing, said first bladder having an expanded shape approximating the shape of said first outer housing and being spaced from the interior surface of said first outer hosuing a predetermined distance in such expanded shape, said first bladder having a lower perimeter;

means for attaching the lower perimeter of said first said bladder at a point opposite said first base to the interior of said first housing, the remainder of said bladder being free to expand and collapse under control of fluids supplied to and removed form the reion contained within the interior of said first bladder between said first bladder and said first base; a second outer housing having a shape approximating the combined outer shape of a natural cardiac ventricle and its associated auricle; said second housing having a second flat base attached to said second housing and attached to said first flat base;

a second flexible bladder in said second housing, said second bladder having an expanded shape approximating the shape of said second outer housing and being smaller in size than the interior of said second outer hosuing and being spaced therefrom a predetermined distance, said second bladder having a lower perimter;

means for attaching the lower perimter of said second bladder to said second base; and means for attaching said second bladder to the interior of said second housing at a point opposite said second base, so that the remaining portions of said second bladder are free to expand and collapse under control of the supply and removal of fluid from the region within the interior of said second bladder between said second bladder and said second base.

20. The combination according to claim 19 further including means for supplying and removing fluid from the itneriors of said first and second bladder.

21. The combination according to claim 19 whereinsaid first and second housings each is seamless except where each of said housings is attached to each said bases.

22. The combinations according to claim 19 further including means for supplying and removing fluid to and from the interiors of said first and second bladders said means comprising first and second conduits passing through said first and second outer housings and into the interiors of said second bladders, respectively, at the places where each of said bladder is attached to the interior of each of said housings.

23. The combination according to claim 22 wherein said first and second conduits comprise first and second drive line connectors, and further including first and second support means extending between said first and second bases and said first and second drive line connectors, respectively, at the points where said first and second bladders are attached to the interiors of said first and second housings.

24. The combination according to claim 19 wherein each of said first and second outer housings has first and second openings therethrough; and further including first and second valves mounted respectively in said first and second openings in each of said first and second housings, wherein said first valve in each of said housings functions to admit blood therethrough into such housing and said second valve functions to permit the passage of blood out of such housing.

25. The combination according to claim 24 further including coupling means for attaching an artery to said second opening in each of said housings and for attaching a vein to said first openings in each of said housings.

26. The combination according to claim 25 wherein said coupling means comprises first and second cylindrical projections attached to each of said outer housings surrounding said first and second openings therethrough, respectively.

27. The combination according to claim 26 wherein said first and second outer housings are fabricated substantially of rigid polyurethane, and said first and second bladders are made substantially of flexible polyurethane.

28. The combination according to claim 27 wherein said first and second bladders include flexible reinforcing mesh embedded in said flexible polyurethane.

29. The combination according to claim 28 wherein said means for attaching the lower perimeter of said first and second bladders to said first and second bases comprises bonding the polyurethane material of the lower perimeter of said first and second bladders to said first and second bases, respectively.

30. The combination according to claim 29 further including a passage through said first and second bases for provdiing common fluid communication therethrough for the transfer of fluid between the interior of said first and second bladders to expand one of said bladders and remove fluid simultaneously from the region beneath the other of said bladders to collapse said other bladder and vice versa.

31. The combination according to claim 30, wherein aid common fluid communication comprises an opening between said first and second bases; and further including means mounted in said opening for transferring fluid back and forth through said opening at a predetermined cyclical rate.

32. The combination according to claim 31 wherein said means for transferring fluid comprises reversible pump means.

33. The combination according to claim 32 wherein said reversible pump means includes an impeller and an electric motor for rotating said impeller.

34. The combination according to claim 33 wherein the shape of said first and second outer housings is substantially ellipsoidal in cross-sections taken along a longitudinal direction and is substantially circular in cross-sections taken along the transverse dimension thereof, and wherein said first and second flat bases are in a plane parallel to said longitudinal cross-sections.

35. The combination according to claim 29 further including a passage through said first and second bases for provdiing common fluid communications therethrough for the transfer of fluid between the interior of said first and second bladders to expand one of said bladders and remove fluid simultaneously from the region beneath the other of said bladders to collapse said other bladder and vice versa.

36. The combination according to claim 35, wherein said common fluid communication comprises an opening between said first and second bases; and further including means mounted in said opening for transferring fluid back and forth through said opening at a predetermiend cyclical rate.

37. The combination according to claim 36 wherein said means for transferring fluid comprises reversible pump means.

38. The combination according to claim 37 wherein said reversible pump means includes an impeller and an electric motor for rotating said impeller.

39. The combination according to claim 19 wherein said first and second outer housings are fabricated substantially of rigid polyurethane, and said first and second bladders are made substantially of flexible polyurethane.

40. The combination according to claim 39 wherein said first and second bladders include flexible reinforcing mesh embedded in said flexible polyurethane.

41. The combination according to claim 40 wherein said means for attaching the lower perimeter of said first and second bladders to said first and second bases comprises bonding the polyurethane material of the lower perimeter of said first and second bladders to said first and second bases, respectively.

42. The combination according to claim 19 wherein the shape of said first and second outer housings is substantially ellipsoidal in cross-sections taken along a longitudinal direction and is substantially circular in cross-sections taken along the transverse dimension thereof, and wherein said first and second flat bases are in a plane parallel to said longitudinal cross-sections.

* * * * *